United States Patent [19]

Kidd et al.

[11] Patent Number: 5,540,892
[45] Date of Patent: Jul. 30, 1996

[54] URINALYSIS COLLECTION AND TESTING KIT AND METHOD

[76] Inventors: Marvin L. Kidd, 3450 Clar-Von Dr., Dayton, Ohio 45430; Barbara J. Bailey, 4350 E. State Rte. 571, Tipp City, Ohio 45371

[21] Appl. No.: 261,450

[22] Filed: Jun. 17, 1994

Related U.S. Application Data

[63] Continuation of Ser. No. 52,124, Apr. 22, 1993, abandoned.

[51] Int. Cl.⁶ ............................... G01N 1/10; G01N 1/18
[52] U.S. Cl. ..................... 422/104; 422/99; 422/100; 422/102; 436/174; 436/180; 141/114; 604/317; 604/321
[58] Field of Search ............................. 422/99–104, 63; 636/174, 180, 807, 810; 141/114, 21; 604/317, 321

[56] References Cited

U.S. PATENT DOCUMENTS

| | | | |
|---|---|---|---|
| 2,267,290 | 12/1941 | Somerville et al. | 149/5 |
| 3,546,334 | 12/1970 | Lerner et al. | 424/3 |
| 3,579,303 | 5/1971 | Pickering | 422/102 |
| 3,620,679 | 11/1971 | De Vaughn | 422/102 |
| 3,660,033 | 5/1972 | Schwartz | 422/102 |
| 3,690,836 | 9/1972 | Buissiere et al. | 422/102 |
| 3,859,671 | 1/1975 | Tomasello | 4/110 |
| 3,982,898 | 9/1976 | McDonald | 23/259 |
| 3,997,656 | 12/1976 | Wertlake et al. | 424/3 |
| 4,265,118 | 5/1981 | Griesel | 73/427 |
| 4,473,530 | 9/1984 | Villa-Real | 422/58 |
| 4,510,621 | 4/1985 | Sak, et al. | 383/89 |
| 4,938,928 | 7/1990 | Bost | 422/100 |
| 4,973,450 | 11/1990 | Schlü ter | 422/101 |
| 5,002,623 | 3/1991 | Steer et al. | 156/221 |
| 5,030,421 | 7/1991 | Muller | 422/102 |
| 5,176,665 | 1/1993 | Watanabe et al | 604/317 |
| 5,183,742 | 2/1993 | Omoto, et al. | 435/14 |
| 5,284,772 | 2/1994 | Oxley | 436/47 |
| 5,364,598 | 11/1994 | Oxley | 422/102 |

OTHER PUBLICATIONS

Burrows, "A New Fixative and Technics for the Diagnosis of Intestinal Parasites,"Technical Bulletin of the Registry of Medical Technologies, vol. 37, No. 8, pp. 208–212 (1967).
Brooke, "PVA–Fixative Technique in the Laboratory Confirmation of Amoebiasis," Triangle 4: 326≧33 (1960).
Hague et al. "Clinical Comparison of a Formaldehyde Free Histological Fixation to Neutral Buffered Formalin," Abstract submitted to the International Academy of Pathology, Sept. 1992.
Meridian Diagnostics, Inc, Product Bulletin for Para–Pak™ (SaF Fixative), 1979.
Sapero et al. "The 'MIF' Stain–Preservation Technic for the Identification of Intestinal Protozoa," Am. J. Trop. Med. Hyg. 2:613–619 (1953).
Notox® Product Brochure.

*Primary Examiner*—James C. Housel
*Assistant Examiner*—Long V. Le
*Attorney, Agent, or Firm*—Thompson, Hine & Flory

[57] ABSTRACT

The invention is directed to a method for removing an aliquot of a liquid sample from an analytical bag containing the liquid sample in which the analytical bag is placed on a base having an aperture; an aliquot of sample is isolated from the balance of liquid sample in the bag by compressing the bag with a collared element surrounding the aperture; the isolated aliquot is compressed by the collared element into the aperture so that the compressed sample causes the bag to rupture spilling the aliquot of sample through the aperture; the sample is collected; and a seal is formed in the bag between the rupture area and the balance of sample in the bag.

4 Claims, 5 Drawing Sheets

URINALYSIS COLLECTION AND TESTING KIT AND METHOD

This application is a continuation of U.S. patent application Ser. No. 08/052,124, filed Apr. 22, 1993, now abandoned.

The present invention relates to a kit for collecting, transporting, testing and archiving urine samples, and to certain elements of that kit.

Current urinalysis kits often include a collection cup for collecting the urine sample, a closable bottle or vial to which the urine sample is transferred and transported to a laboratory at which it is tested, and a bag member into which the bottled sample is placed and sealed for shipment to the laboratory. In order to insure sample integrity, these kits may include various seals which prevent tampering and labels which identify the samples and their associated paperwork.

While the urine collection kits described above have been widely used for a long period of time, they are extremely inconvenient for several reasons. Typically, the collection cups and bottles are manufactured and shipped to a location where the cups and bottles are assembled into a kit with instructions and forms. The cups can be stacked for shipment, but the bottles usually must be shipped in trays or flats resulting in large shipping volumes. These large shipping volumes become even larger when the cups and bottles are assembled into individual kits. These kits are individually boxed or bagged for further shipment to the collection site. The kit assembler must maintain large storage areas for the inventory of cups and bottles used in the kits and at the collection site large areas must also be maintained to store the assembled kits.

An examination of these urine sampling and collection techniques shows that this industry is spending substantial monies to ship large volumes of empty and substantially empty containers and that substantial monies could be saved if a compact and more efficient means were available to collect and ship urine specimens.

In addition to the shipping inconveniences discussed above, a further inconvenience of some kits is that a quantity of the urine sample must be removed from a vial at the laboratory and placed in a test tube for analysis. This step is labor intensive and adds additional expense to the urinalysis. In many cases, the test tubes are generally used once and discarded to prevent any possibility of contamination. Finally, it is now the standard laboratory practice to store those samples which give a positive test result in a freezer for up to a year in the event further verification of test results is required. This adds the further expense of large volumes of expensive refrigerated storage space to the cost of the analysis.

In view of the disadvantages of current urinalysis kits, an improved kit which reduces the large shipping and storage volumes currently required and reduces or eliminates some of the handling costs would be desired.

SUMMARY OF THE INVENTION

The present invention provides a urinalysis kit and a method employing the same in which the urine sample is collected, enclosed and shipped in bag members. These bag members can be shipped flat or essentially flat thereby reducing substantially the shipping costs and inconveniences of kits which employ collection cups and bottles.

In accordance with one aspect of the invention, the urine sample is collected in a bag member which is formed from two interfacing flexible members and is provided with a reinforcing member adjacent its opening. The reinforcing member facilitates holding the bag during urination. In accordance with one embodiment of the invention, the bag is provided with a rigid support panel, adhered thereto, which can be bent with hand pressure to hold the bag open during urination. In accordance with another embodiment of the invention, the reinforcing member is a plastic bead and still more preferably a bead which is designed to interlock and seal the bag when pressure is applied to the bead. In accordance with another embodiment, a pair of reinforcing members may be provided adjacent the periphery of the opening which are spaced from one another so as to permit the bag to be held by placing the index finger and thumb between the reinforcing members. In a still further embodiment of the invention a temperature strip is provided on the bag to measure urine temperature and thereby verify its authenticity. See U.S. Pat. Nos. 4,408,905 and 4,564,299 to Ehrenkrantz. Alternatively, a heat sensitive film, which changes color when a threshold temperature indicative of urine authenticity is reached, may be used. As a further modification, the collection bag may be printed to show the volume of urine deposited in the bag and/or the maximum and minimum volumes to which the bag should be filled.

Another aspect of the invention is an analytical bag for use in analyzing and retaining a split sample. The bag is formed from two interfacing flexible members sealed at their peripheries and the sealable bag has a slit therein for introducing a urine specimen. In one embodiment, this bag is sealed internally of the periphery so as to form an elongated test tube like chamber therein for receiving about 3 to 10 ml of urine. In another embodiment, the sealable bag member (hereinafter referred to as an archival bag) accommodates a larger sample of urine such as 10 to 30 ml. The volumes stated herein are the volumes of urine deposited in the bag members. The bag members will actually accommodate much larger volumes than the stated volumes such that if pressure is applied to the bag member during shipment, the fluid under pressure in the bag will not cause the bag to rupture.

A pressure sensitive adhesive is provided along the upper portions of the bag members such that the upper portions can be folded to cover the opening slits and provide fluid tight seals around them. Of course, those skilled in the art will appreciate that the invention is not limited to the use of an adhesive to provide a fluid tight seal, but any means which provides a fluid tight seal may be used. For example, the slits may be sealed using any pressure sensitive adhesive tape that is suitable for the purpose. Alternatively, the portions of the bag members below the slits may be sealed off from the slits by forming a heat sealed seam between the slits and the lower portions of the bag members.

The analytical and archival bag members may be used together and connected along one of their edges with a line of perforations preferably provided between their adjacent sealed peripheral edges to facilitate their separation and subsequent use in analysis as described below. It is advantageous to include the analytical and archival portions as part of a unified bag member because it reduces the opportunity that the analytical bag member may be associated with the wrong archival bag member or vice versa.

In accordance with the invention, the analytical bag member may be used directly to analyze the urine sample without transferring the sample to a test tube. The bag may be opened by cutting or removing the upper portion thereof along a line below the fluid tight seal. A notch or perforation line may be provided if it is desired to be able to tear the bag member open. The opened bag is then supported in an analytical tray or rack in a manner analogous to the test tubes used in conventional analyzers whereupon a sample is withdrawn and analyzed in an otherwise conventional manner.

The archival bag member can be retained and used to verify results, for example, in the event of a positive indication of drug usage or the like. By providing separate archival and analytical bags, government requirements for two separate specimens may be satisfied.

As a further alternative, the analytical and archival bag members do not have to be torn to withdraw the sample. A hypodermic needle can be inserted through the wall of the bag and into the urine to withdraw a sample for testing directly.

The kit may further include a shipping bag member of the type described in U.S. Pat. No. 4,510,621 to Sak et al. or bag members of other designs to mail or otherwise ship the analytic portion and the archival portion of the bag member and associated paperwork to the lab for analysis.

For shipment to the collection site, the collection bag, the analytical and archival bag and the shipping bag may be assembled and packaged in any convenient manner. For example, they may be placed flat on an appropriate backboard and sealed within a conventional heat shrinkable wrapping material.

Finally, the invention provides an apparatus for removing the sample from the specimen containing bag. The apparatus includes a collar which moves into contact with the bag to secure it in position over an aperture in a base. As the bag is maintained in position by the collar, a plunger moves into contact with the bag causing it to rupture. The specimen flows through the rupture hole, through the aperture and out into a test tube or other similar device for collection. The bag can then be resealed and the specimen stored for future use.

DETAILED DESCRIPTION OF THE INVENTION

Figure 1:
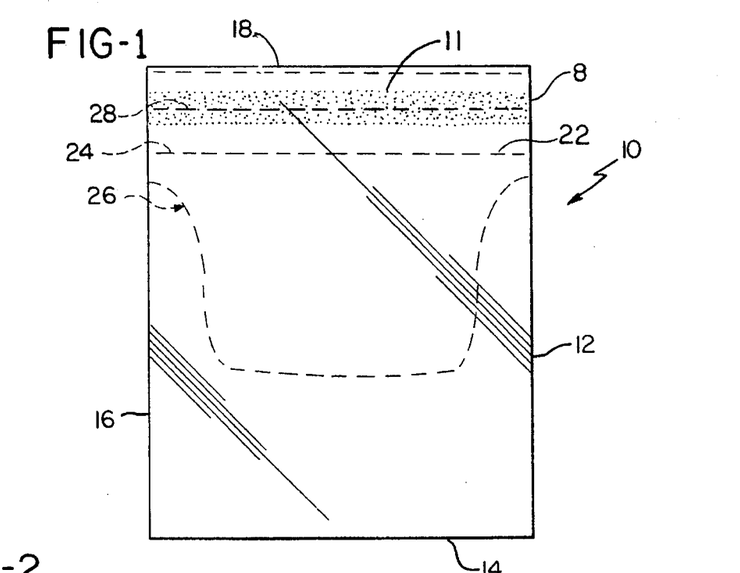
FIG. 1 is a front view of a collection bag useful in the present invention.

FIG. 1 illustrates a collection bag useful in the present invention. The bag may be formed from any conventional flexible sheet known in the art including, but not limited to, paper, treated paper, polyethylene, polypropylene, polyester (PET), saran, or the like. Metal-backed or aluminized films may also be useful. The bag should be formed from a material that is inert in the urinalysis, e.g., a material which does not adsorb any of the chemical markers which are the target of the analysis. HDPE or polypropylene may be useful for this purpose. Polypropylene 326 and 362 from James River Corp. may also be useful. It has been found that some plastic films include an anti-blocking layer to prevent the film from sticking. In selecting a film for use in the bag, it is critical that the anti-blocking layer not interfere with the integrity of the analysis by interacting with any of the compounds being analyzed.

The bag 10 includes two interfacing flexible members (one shown) which are sealed together at their respective edges 12, 14, 16 and 18, to form bag 10. A conventional technique such as heat sealing may be used to seal the edges. One of the flexible members is provided with a slitted opening 22 formed by means of a line of perforations 24 to assist in opening the bag 10.

As illustrated in FIG. 1, the bag 10 includes an optional panel member 26 which facilitates holding the bag 10 during urination. In the preferred embodiment, this reinforcing member is a rigid panel such as cardboard. This rigid reinforcing panel 26 is attached to the bag 10 by a common adhesive which is compatible with the material from which the bag is formed. Rubber cement may be useful. The panel 26 is attached to the flexible member which does not contain the slitted opening 22. Preferably, the panel 26 should be capable of being bent by hand pressure so that the opening slit 22 can be maintained in an open position while the specimen is introduced into the bag 10. In a preferred embodiment, the reinforcing panel 26 is contoured so that it fits comfortably in the palm of a hand. Further, the reinforcing panel 26 may include a fold line 28 which facilitates sealing the bag 10 when the panel 26 is folded about the line 28 to seal the slit 22. Finally, the backside of the reinforcing panel 26, i.e., the side which is not adhered to the bag 10, may be printed with a form to include identifying information, such as name, date and address of the test subject.

The upper portion 8 of the flexible member having slit 22 is coated with a pressure sensitive adhesive 11 which is covered with a release film (not shown). After the sample has been deposited in the bag 10, upper portion 8 of bag 10 is folded along line 28 of panel 26, so as to form a fluid tight seal once it contacts the flexible member and covers slit 22. A tamper evident label may be applied to the bag to verify sample integrity.

Figure 10:
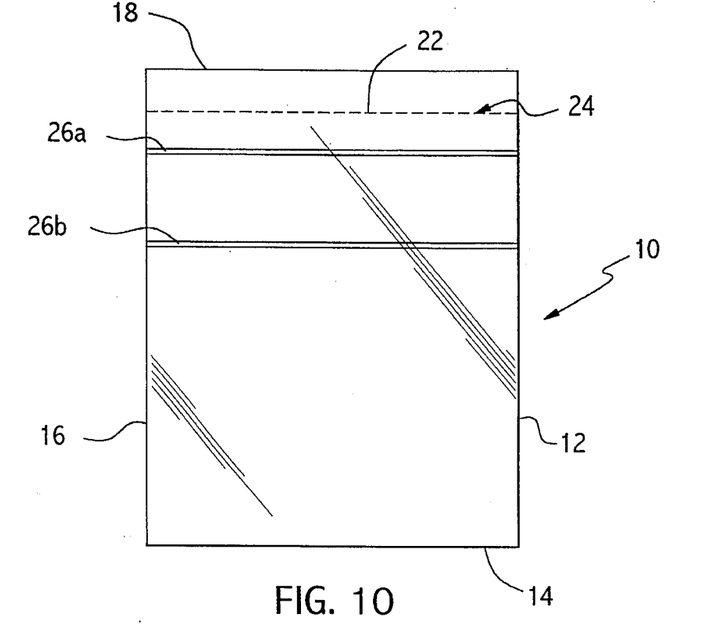
FIG. 10 is a front view of a collection bag in accordance with another embodiment of the invention.

In an alternate embodiment, as shown in FIG. 10 to facilitate holding the bag during urination, the reinforcing member may be a plastic bead 26a. This bead may be provided on the inside surface of the front flexible member and optionally may be designed to interlock with a compatible bead member (not shown) provided on the inside surface of the back panel. Such interlocking beads are commonly used in the art relating to closable storage bags, one such bag being sold under the trademark ZIPLOC®. In another embodiment, a second reinforcing bead 26b may be provided in the bag such that the finger and thumb of one hand can be placed between the members on the outside of the bag 10 to hold the bag 10 during collection. The bag 10 can be sealed as described previously and analyzed as described later or the bag 10 can be used for collection only and easily formed into a spout to facilitate transfer of the urine to the analytical and archival bags as discussed below.

To ensure that the test subject deposits the proper volume of urine into the bag 10, the bag 10 can be marked with volume indicators such as maximum and minimum fill lines. The volume indicators are located at an appropriate position on either the front or rear flexible member and preferably on the front flexible member. These lines would enable the test subject to deposit the necessary quantity of urine to provide a proper amount for test samples and also to ensure that the bag 10 would not be over filled to a point which would jeopardize the integrity of the sealed bag 10.

To verify sample integrity, a thermometer or a temperature-sensitive strip may be placed on one of the flexible members near at the bottom of the bag 10 to measure or detect the temperature of urine deposited in the bag 10 and thereby verify that the urine is fresh urine and is not a substitute. Temperature strips useful in the invention are well known in the art. One example is commercially available under the designation Diagnostic Digital Indicator from American Thermal Instruments. When the specimen needs to be preserved for shipment and analysis at a central lab, a preservative tablet may be provided with the bag. The outside of the bag may also be spot-printed with a signature block in the form of a printable or writable spot coating of a white or opaque pigment.

To provide for proper sample identification, a bar code label can be affixed to the bag 10. This bar code label allows for electronic processing of the sample and for use with the automated processing system described below. The bar code would also help to eliminate misidentification or confusion of samples.

Figure 11:
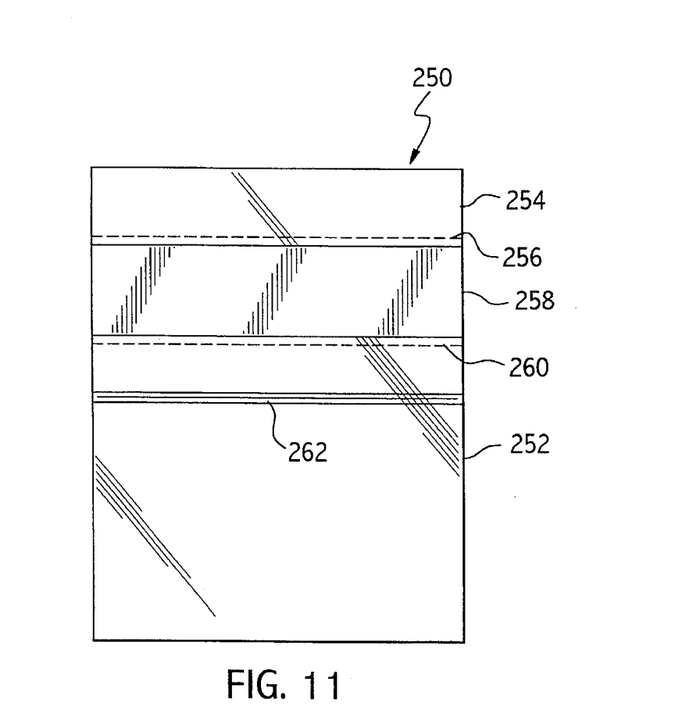
FIG. 11 is a front view of another collection bag in accordance with the invention.

Another collection bag useful herein is shown in FIG. 11. This bag is designated 250 and is sealed along each of its four sides 252 to prevent tampering with the bag. To use the bag, the top portion 254 is removed along perforation line 256. The bag 250 is then opened and held for introduction of the fluid sample with the aid of reinforcing panel 258 which may be cardboard and provided on the front and/or back of the bag. After the sample has been deposited in the bag 250, the reinforcing panel 258 and the underlying portion of the bag can be removed along perforation 260. The sample can be sealed in the bag by interlocking bead 262.

Figure 2:
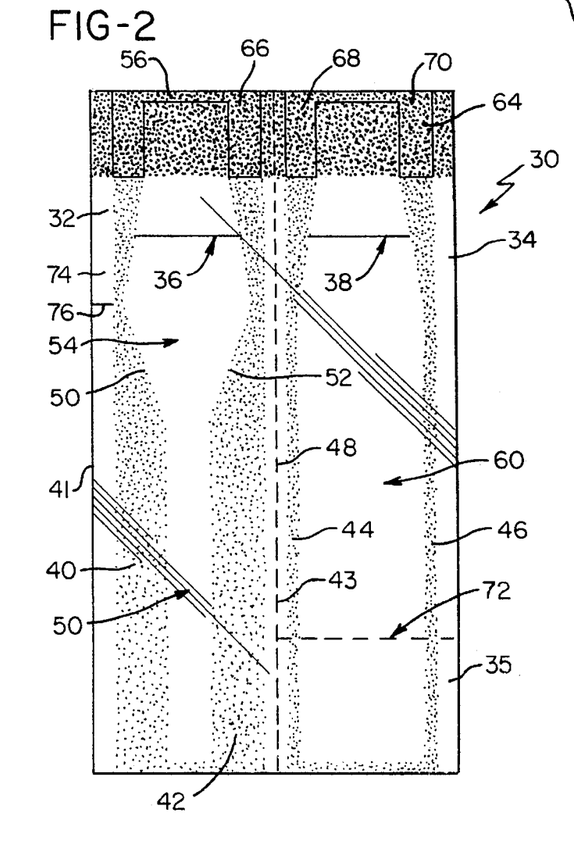
FIG. 2 is a front view of analytical and archival bag useful in the invention which are attached at their periphery.

FIG. 2 is a frontal view of a member 30 for use in an alternative embodiment of the invention. The member 30 includes an analytical bag 32 and an archival bag 34 and can be formed of any of the plastic films suitable for the purposes described herein and available in the art. A particularly useful film is a polyolefin. The bag members may be formed of an inert material such as HDPE or polypropylene as discussed previously for the collection bag.

The member 30 includes a first analytical bag 32 and a second archival bag 34. The member 30 is formed from a first and second interfacing flexible member and is sealed in any conventional manner at each of its four peripheral edges except where the edge may be formed by a fold between the first flexible member and the second flexible member and even then, for integrity, it may also be desirable to seal the edge.

Transverse slits 36 and 38 are provided in each of bags 32 and 34 on either the first or second flexible members to provide access for pouring the collected urine into the members. Preferably, the longitudinal seals 40, 42, 44 and 46 are inset slightly (e.g., about ⅛ to ¼ inch) from the edges of each member. A line of perforations 48 may be provided in each of the first and second members between bags 32 and 34 to facilitate their separation.

Seals 40 and 42 in the analytical bag 32 extend inwardly of the longitudinal edges 41 and 43 of the bag 32 to form an analytical chamber 50 which is dimensioned to hold about 3 to 10 ml and preferably about 5 ml. of the specimen. This chamber may be about 0.75 inch in diameter. The actual volume of the analytical bag will be much larger (e.g., possibly 2 to 3 times larger than the specimen volume it is designed to hold). In this manner, the analytical bag 32 is unlikely to be ruptured if the urine sample is placed under pressure during shipment. Seals 40 and 42 taper outwardly at 50 and 52 to form a funnel-like portion 54 for filling the chamber 50. Above the funnel portion 54, seals 40 and 42 may progress inwardly until they join the seal 56 at the top of bag 32.

Archival bag 34 is designed and dimensioned to hold about 10 to 30 ml. of sample. The volume of chamber 60 will be much larger than 10 to 30 ml. such that the member 34 is less likely to rupture if pressure is applied to archival member 34 during shipment.

In the upper portion of the archival bag 34, the seals 44 and 48 taper inwardly until they join with the top seal 64.

The upper portions 66 and 68 of members 32 and 34 are coated with a pressure sensitive adhesive 70 which is covered with a release film (not shown). After placing sample in bags 32 and 34, portions 66 and 68 may be folded over slits 36 and 38 so as to form a fluid-tight seal. As previously mentioned, other means may be used to form a fluid-tight seal. In particular, the adhesive may be eliminated on the upper portions of members 32 and 34 if a separate pressure sensitive adhesive tape is applied to seal the slits 36 and 38. Alternatively, the slits 36 and 38 may be sealed off from the lower, sample-containing portions of the bag using interlocking beads, as described above, or by forming a heat sealed seam.

In some cases, it may be desirable to duplicate member 32 so as to form the bag with two analytical portions. In this manner, in the event of a positive test result, a second analytical sample will be immediately available to verify the test results without invading the archival member 34. Alternatively, a 5 ml portion of the urine specimen can be located at the bottom of the member 34 and sealed off from the balance of the archival specimen at the laboratory by performing heat sealing along line 72. The specimen can then be removed from the lower portion of the bag and the balance of the specimen can be retained uncontaminated for archival purposes.

At the laboratory, the analytical bag or bags 32 are separated from each other and from the archival bag 34. The upper portion 74 of the analytical bag 32 may be removed by cutting or tearing with the aid of optional notch 76 to open the analytical member 32. The open member 32 is supported in a test tube or analytical tray of the type conventionally used in commercial laboratories such that the sample can be analyzed directly. In this manner, the need to transfer sample to test tubes is eliminated thereby eliminating one of the most labor intensive and time-consuming aspects of the analysis. A bar code member or other automated scannable tag may be placed on the analytical 32 and archival 34 bags to reduce the likelihood of human error by possibly eliminating the need to record the number and slot into which each sample is deposited in the analyzer. Preferably, these steps are automated. That is, the analytical bag 32 can be automatically cut open and deposited in an analytical tray for use in the analyzer. Alternatively, the analytical member 32 can be directly deposited unopen in a tray, the tray can be scanned to identify the samples, and the specimens can be withdrawn using an automated syringe which punctures the bag 10 and removes the volume required for analysis.

Figure 3:
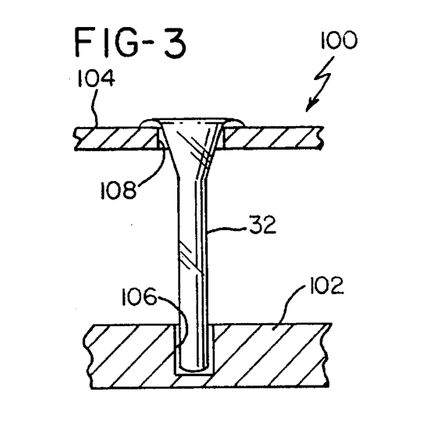
FIG. 3 illustrates the use of the analytical bag in a test tube rack.

FIG. 3 illustrates a portion of a conventional analytical tray or test tube rack 100 having a base member 102 and an upper support rack 104. The base 102 has a circular cavity 106 and the rack 104 has an aperture 108 for supporting a test tube. In accordance with the invention, the analytical bag 32 is opened and inserted into the rack 100 whereupon the sample is processed in a conventional manner. The bag 32 may be supported by draping the upper portions of the bag over the upper rack 104. A label (not shown) may be adhered to the body of bag 32 which identifies the sample and assists in supporting the bag in the rack 100.

Figure 4:
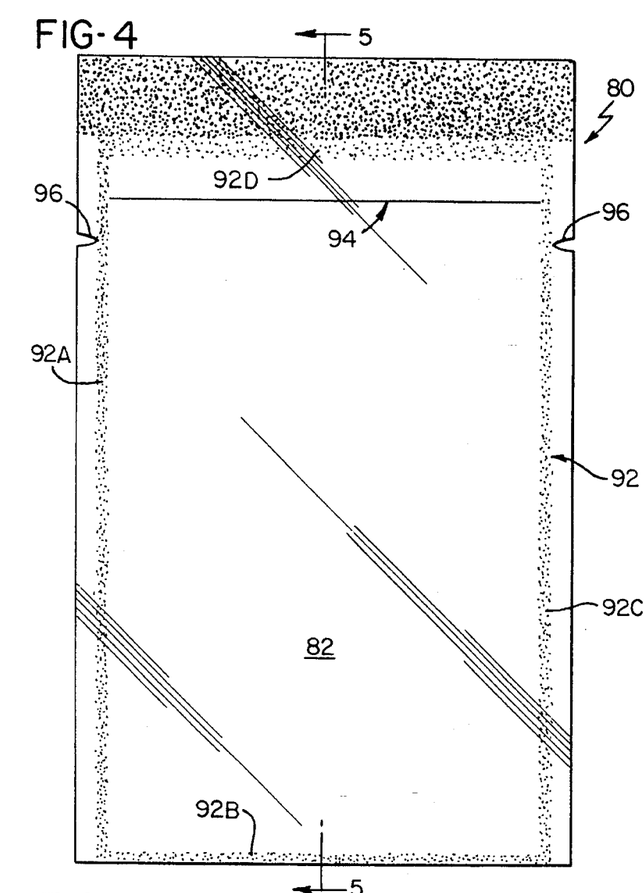
FIG. 4 is a front view of a shipping bag useful in the invention.
Figure 5:
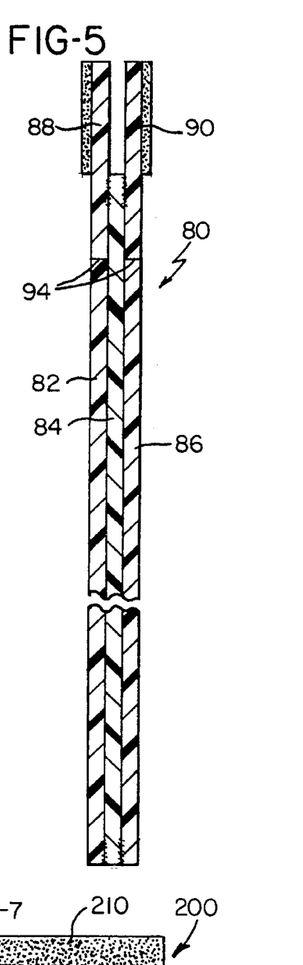
FIG. 5 is a cross-section of the bag of FIG. 4 along the line 5—5 in FIG. 4.

FIG. 4 illustrates a bag 80 which can be used to ship the analytical and archival bags 32 and 34 as well as supporting documentation to the laboratory. A cross section of the bag 80 is shown in FIG. 5. The bag 80 includes three interfacing flexible members 82, 84, 86, preferably of a plastic film such as polyethylene or another film which can be used for the purpose. The front member 82 and the back member 86 extend beyond the upper portion 85 of the middle member 84 as shown at 88 and 90. Each of the front and back members 82 and 86 is sealed to the periphery of the middle member as shown at 92a, 92b, 92c and 92d in FIG. 4. Each of the front and back members 82 and 86 includes a slit 94 and 98, respectively, which extends less than the width across the bag 80. End portions 88 and 90 of the front and back members 82 and 86 are provided with a pressure-sensitive adhesive such that they can be folded over the slits 94 and 98 in the front and back members 82 and 86 to form a tamper resistant seal. The adhesive will be protected by a release film, not shown, prior to use. A notch 96 may be provided in the edge of the bag 80 to facilitate opening.

Figure 6:
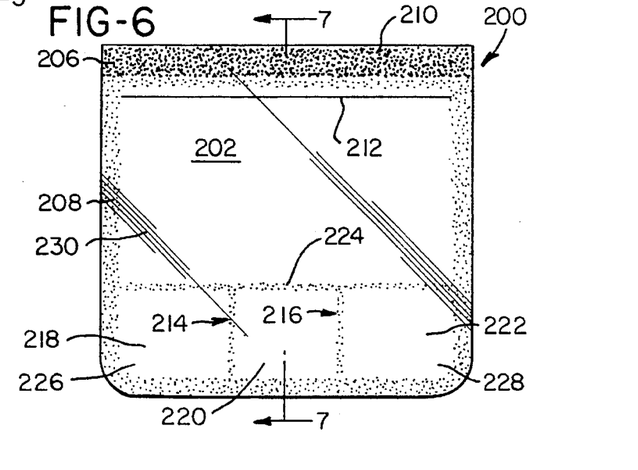
FIG. 6 is a front view of an alternative collection bag design.
Figure 7:
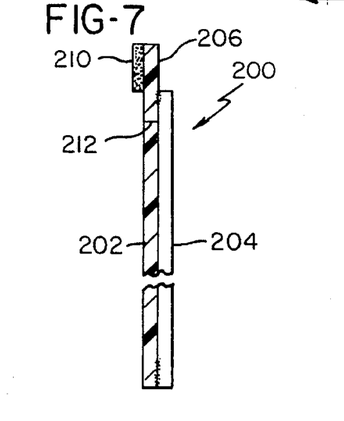
FIG. 7 is a cross-section of the bag of FIG. 6 along the line 7—7 in FIG. 6.

FIG. 6 illustrates a further embodiment of the invention in which a collection bag 200 is shown. The collection bag 200 is formed from two interfacing flexible members 202 and 204, preferably made of plastic as previously identified for the collection bag 10. The front member 202 is larger than the back member 204 and includes a portion 206 which extends beyond the peripheral (top, bottom and sides) seal 208. Portion 206 is preferably provided with a pressure sensitive adhesive 210 but other sealing means or agents could be used. A slit 212 is provided in the front member 202 to provide access for depositing the urine. Slit 212 does not extend beyond the peripheral seal 208 and may be such shorter dimension as is functional for the purpose. Before or after urination, one or more partial seams 214 and 216 are formed in the collection chamber which intersect seam 208 at the base of the collection chamber to provide two or more chambers 218, 220 and 222 for receiving predetermined analytical quantities of urine, for example, 5–10 ml to provide a split sample. After urination, these chambers may be heat sealed or otherwise sealed by seam 224 to provide segregated analytical quantities of urine in the collection bag. The signature block may be applied to this portion of the bag to thereby label the split sample. Heat sealing to form analytical quantities is accomplished as described next.

The volume of the collection bag 200 is greater than the volume of urine deposited in the bag 200, preferably by a factor of three times. Slit 212 is sealed by folding the flap 206 with adhesive 210 over the slit 212 (or a separate adhesive tape may be used). With the bag 200 sealed, the bag 200 may be placed between a pair of heated elements to form seams 214, 216 and 224 therein. A portion of the sample in the bag 200 may be collected in the corner 226 of the bag 200 so that it is not affected by any heating. Thereafter, sample may be collected in corner 228 of the bag 200 and seam 216 formed. With seam 214 and 216 formed, sample will automatically fill the inner chamber 220 and the three chambers can be sealed by displacing the analytical quantities in chambers 218, 220 and 222 away from the heating element as seam 224 is formed.

In another embodiment of the invention, the collection bag 10 may be formed with seams 214 and 216 already therein. After urine is deposited in the bag, the urine is displaced to the bottom of the chambers and the seal 224 is formed. The remaining urine above seal 224 may be used for archival purposes or as a second sample.

In both embodiments described above, the bulk of the urine specimen remains in the upper chamber 230 formed between peripheral seam 208 and seam 224.

In use, chamber 218 may be punctured with a hypodermic needle and the sample removed, spilled or pressed therefrom into a test tube or other analytical element. Alternatively, chamber 218 can be excised from the collection bag. In this case, seams 214, 216 and 224 may be parallel double seams which permit the bag to be cut without spilling its contents. The excised chamber may be deposited into a test tube where it is punctured by a hypodermic needle and a sample withdrawn. Other means of opening the chamber element may also be used. If additional analyses are required, chamber elements 220 and 222 may be excised and/or opened in a similar manner. The urine in chamber 230 can be archived.

While the bag 200 has been described with respect to two partial seams 214 and 216 intersecting the seam 208 at the base, those skilled in the art will recognize that the number of these partial seams is a matter of choice. There may be as few as one or as many as desirable.

The sample can be removed from a bag as shown in any of FIGS. 1, 6 and 10 using a variety of techniques. In one case a hypodermic needle can be inserted into the bag or one of its chambers and a sample can be withdrawn. In another case, the bag may be slit at a corner and the sample may be poured from the bag. For example, chamber 226 or 228 in FIG. 6 could be entered in this fashion.

Figure 8:
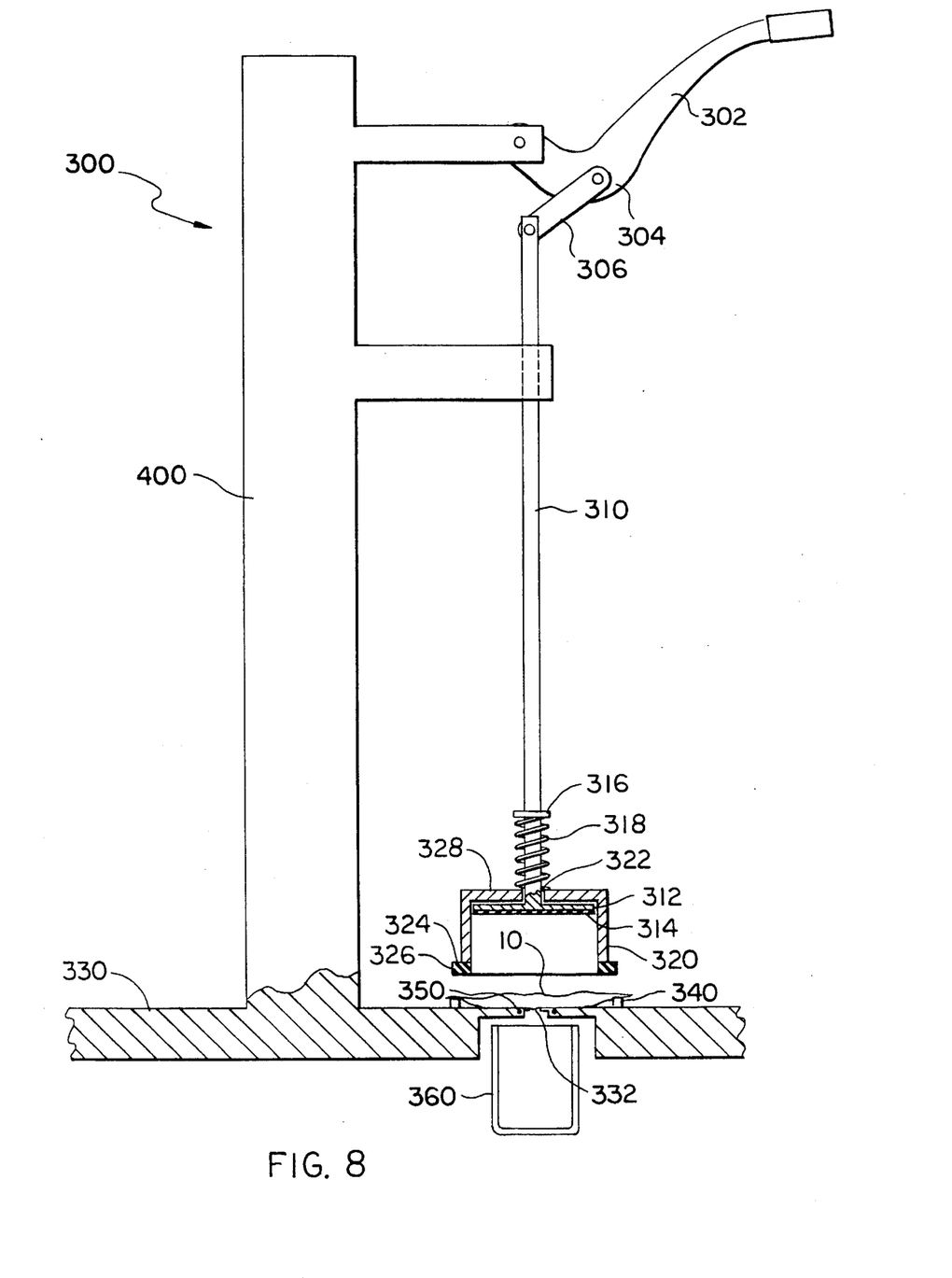
FIG. 8 is a perspective view of an apparatus used to remove samples from the collection bag.

In accordance with a preferred embodiment, an aliquot of sample can be removed from bag 10 by means of a sample removal apparatus 300, as illustrated in FIG. 8. The sample removal apparatus 300 of this invention consists of a lever arm 302 having an elbow 304, a plunger shaft 310, a plunger 312, a compression spring 318, a collar 320 and a vertical support member 400. The entire apparatus 300 is mounted on a base 330 having an aperture 332 therein.

Lever arm 302 has an elbow 304 and is reciprocally mounted on vertical support member 400. Elbow 302 is linked to plunger shaft 310 by elbow link 306. At its end opposite elbow link 306, plunger head 312 is threadly mounted on plunger shaft 310. Plunger head 312 has, on its surface, a compressible padding 314 made from rubber or a resilient foam. Plunger shaft 310 extends through hole 322 in collar 320. Collar 320 is slidably mounted around plunger shaft 310 and retained on plunger shaft 310 by plunger head 312. Mouth 324 of collar 320 has a rubber gasket 326 mounted thereon. Compression spring 318 encircles plunger shaft 310 and rests on shoulder 328 of collar 320. Spring 318 is retained on its upper end by retaining ring 316 on plunger shaft 310 and acts to bias collar 320 toward plunger head 312.

Apparatus 300 can be mounted on a table by securing base 330 thereto. Aperture 332 is located directly beneath plunger head 312 in base 330 and has a diameter of about 0.125 to 0.50 inch. Sealing ring 340 is mounted on base 330, encircles aperture 332 and has the same diameter of gasket 326. A test tube or other receptacle 360 can be placed beneath aperture 332 to collect the specimen as it is removed from bag 10.

Apparatus 300 may also include an electric impulse heat-sealer to seal the bag 10 once it has been opened, as discussed below. The heat-sealer includes a coil 350 which encircles aperture 332 and is connected to an electric source (not shown). Coil 350 has a diameter larger than aperture 332 and smaller than ring 340.

Figure 9:
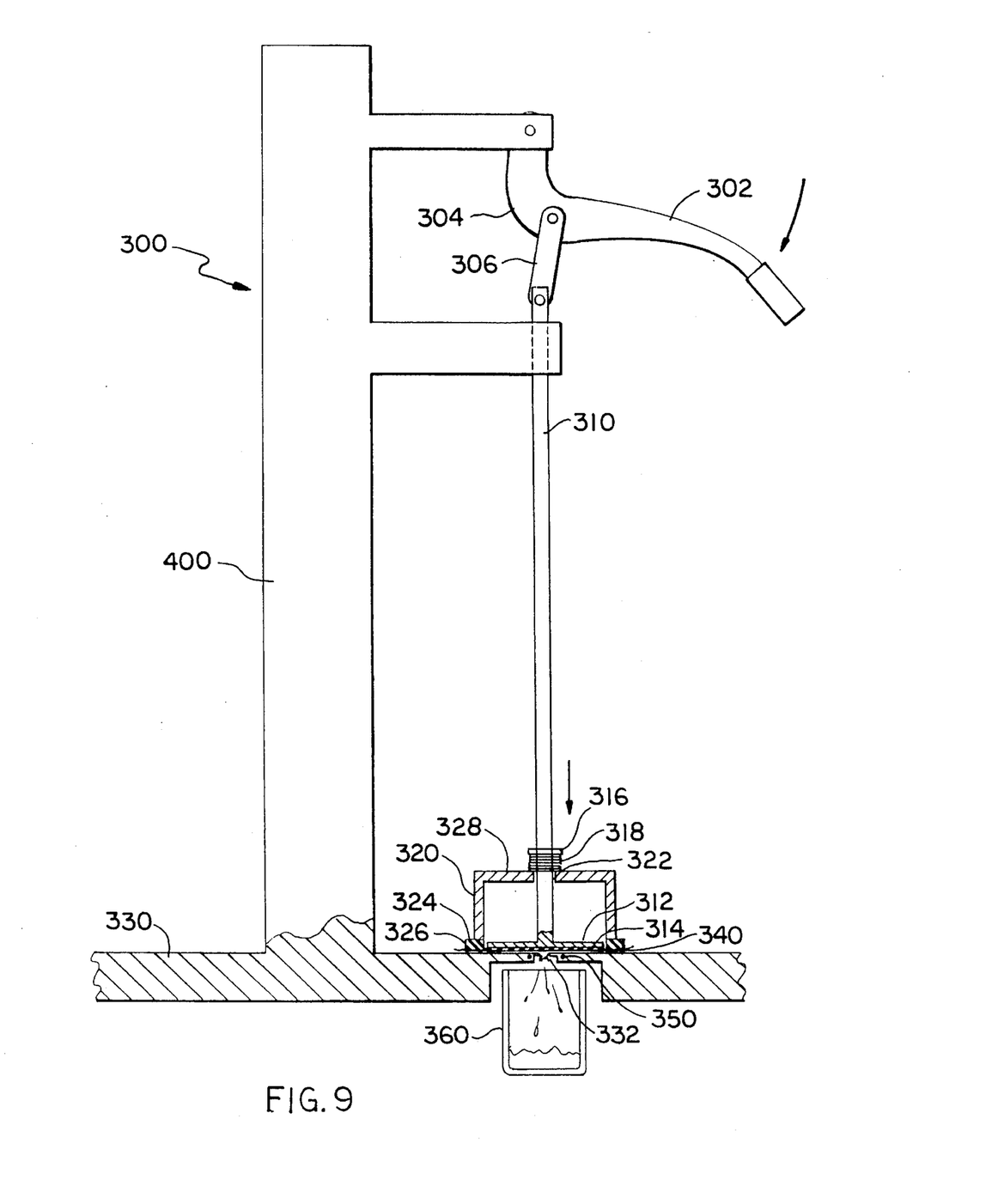
FIG. 9 is a perspective view of the apparatus of FIG. 8 in the position at which the sample is removed from the collection bag.

To release the specimen from bag 10, bag 10 is placed beneath apparatus 300 so that the bag 10 is located beneath collar 320 and the specimen containing portion of bag 10 is located over aperture 332 and rests on sealing ring 340. Lever arm 302 is then reciprocated downwardly toward base 330. As lever arm 302 is reciprocated downwardly, link 306 applies a downward force onto plunger shaft 310. As plunger shaft 310 moves downward, ring 316 forces collar 320 downward by means of spring 318. This causes collar 320 to make a seal with sealing ring 340 securing bag 10 to base 330 and trapping an aliquot of the sample in the sealed area over aperture 332. Collar 320 is held in position to trap the sample in the bag 10 by the downward force of spring 318 which is compressed. As shown in FIG. 9, with continued downward movement of shaft 310, plunger head 312 moves into contact with bag 10 and the aliquot of the sample in bag 10 flows into aperture 332. The plunger 312 forces the specimen to compress and causes that portion of the bag 10 in aperture 332 to rupture and release the specimen. The specimen flows through aperture 332 and is collected in a test tube or other analytical receptacle 360 located beneath base 330. Once the specimen has been removed from bag 10, bag 10 may be resealed. The bag 10 may be resealed using adhesive tape, ultrasonic bonding, heat sealing, or any other conventional sealing method.

To reseal the bag 10, apparatus 300 may also include an impulse heat-sealer which acts to seal bag 10 once the specimen has been released. The heat-sealer can be actuated by means of a switch (not shown). When the heat-sealer is actuated, an electric current causes coil 350 to heat rapidly. As coil 350 heats, it causes the first and second interfacing panels around aperture 332 to melt together and form a seal around the ruptured area. This provides a complete seal around the ruptured area which permits bag 10 to be used to store the sample for subsequent retesting and verification if necessary.

In a preferred embodiment, lever arm 302 and link 306 can be replaced by an automatic means for reciprocating plunger 310. In this preferred embodiment, they would be replaced by a hydraulic cyclinder, a pneumatic cylinder or a solenoid.

Other means of removing the sample are also available including heat sealing the bag to form a test-tube shaped chamber which can be removed from the bag and inserted into an analytical tray in a conventional manner. A sample can be removed from the bag encapsulated in the film forming the bag by isolating a portion of the fluid in the bag and heat sealing the portion around its perimeter to form a sealed body which can be removed from the bag. The encapsulated sample can be placed in a test tube and opened for analysis. In both these embodiments, by heat sealing a double seam, the sample can be removed from the bag and the bag remains sealed for archival purposes and to provide a split sample.

Those skilled in the art will appreciate that the following embodiments and manifestations of the invention have been disclosed.

A kit useful in performing urinalysis comprising a first bag into which urine is collected and a second bag to which the urine is transferred for shipment to a laboratory for analysis.

An analytical bag for use in analyzing urine and other fluid specimens which comprises first and second interfacing flexible members, said members being sealed together at their peripheries to form an elongated chamber therein for receiving said specimen, and a slit in one of said flexible members for introducing said specimen into said chamber, said chamber being sufficiently large to accommodate about 3 to 10 ml of said specimen in a substantially vertical orientation, analogous to a test tube, for analysis.

A bag for use in analyzing urine and other fluid specimens, said bag comprising first and second interfacing flexible members, said flexible members being continuously sealed to one another at their peripheries to form a chamber for receiving said specimen, a slit in one of said flexible members for introducing specimen into said chamber, said chamber having at least one partial seam intersecting said peripheral seal at the base of said chamber to form a subchamber for receiving an analytical quantity of said specimen.

In a method for performing urinalysis and analysis of other fluid specimens wherein liquid specimens are placed in a container for transfer to a laboratory for analysis, the improvement wherein said container is a bag member comprising first and second interfacing flexible members, said flexible members being sealed at their periphery to form a chamber for receiving said specimen, a slit is provided in one of said flexible members for introducing said specimen into said chamber and, after introducing said specimens into said container, a fluid tight seal is formed about said slit.

A unified bag member comprising first and second interfacing flexible members, joined at their peripheries, which form a first analytical bag and a second archival bag wherein said first analytical bag is separably attached to said second archival bag along a line of perforations extending vertically from the lower peripheral edge to the upper peripheral edge of said unified bag, said first analytical portion comprising a chamber for receiving a first portion of an urine specimen for analysis and said second archival portion comprising a chamber for receiving a second portion of said urine specimen for archival purposes.

An analytical bag for use in analyzing urine and other fluid specimens which comprises: first and second interfacing flexible members, said members being sealed to one another at their peripheries to form a bag for receiving said specimen; an opening slit in one of said flexible members through which said specimen can be introduced into said bag; a layer of an adhesive provided on one side of said members such that by folding said member along said slitted opening, said slitted opening can be sealed; and a support panel more rigid than said flexible members, adhered to said flexible member not containing said slitted opening, said support panel being bendable by hand pressure such that said opening slit is maintained in an open position while said specimen is introduced to said bag.

A method for analyzing urine and other fluid specimens which comprises: depositing a fluid specimen in a flexible bag formed of thermoplastic film; sealing said bag to contain said fluid specimen therein; heat sealing a seam internally in said bag to isolate a quantity of said specimen for analysis; and removing said isolated specimen from said bag for analysis.

A method for removing an aliquot of a liquid sample from an analytical bag containing the same comprising: isolating a portion of liquid sample in the bag; compressing the isolated portion of the sample within the bag into an aperture such that the bag ruptures and spills the sample through the aperture; and collecting the sample.

Having described the invention in detail and by reference to preferred embodiments thereof, it will be apparent that modifications and variations are possible without departing from the scope of the invention defined in the appended claims.

What is claimed is:

1. A method for removing an aliquot of a liquid sample from an analytical bag containing the liquid sample comprising the steps of:

placing an analytical bag on a base having an aperture therein;

isolating an aliquot of a liquid sample from a balance of liquid sample in the bag by compressing the bag with a collared element surrounding the aperture;

compressing the isolated aliquot of the sample within the collared element into the aperture such that the compressed sample causes the bag to rupture thereby forming a ruptured area and the aliquot of the sample is spilled through the aperture;

collecting the sample; and forming a seal in the bag between the ruptured area and the balance of sample in the bag.

2. The method of claim 1 wherein the step of forming a seal in the bag comprises the steps of applying a heat sealer coil to the bag between the ruptured area and the balance of sample in the bag; heating the heat sealer coil; and melting the bag to form a seal between the ruptured area and the balance of sample in the bag.

3. The method of claim 2 wherein the collared element is mounted on a plunger shaft, the plunger shaft being reciprocally mounted on the base, such that reciprocation of the plunger shaft causes the collared element to isolate the aliquot of sample in the bag from the balance of sample in the bag.

4. The method of claim 3 wherein the step of compressing the isolated aliquot of the sample is performed by a plunger head mounted on the plunger shaft such that, when the plunger shaft is reciprocated, the plunger head compresses the isolated aliquot of sample into the aperture causing the compressed sample to rupture the bag.

\* \* \* \* \*